United States Patent [19]

Dupont et al.

[11] Patent Number: 4,677,056
[45] Date of Patent: Jun. 30, 1987

[54] MONOCLONAL ANTIBODY SUBSETTING HUMAN HELPER AND KILLER T-CELLS AND METHOD

[75] Inventors: Bo Dupont, Harrison; Michael K. Hoffman, New York; Nancy Collins, Larchmont, all of N.Y.; Soo Y. Yang, Brookline, Mass.; Yasuo Morishima, Nagoya; Masahide Kobayashi, Hamamatsu, both of Japan

[73] Assignee: Sloan-Kettering Institute for Cancer Research, New York, N.Y.

[21] Appl. No.: 524,293

[22] Filed: Aug. 18, 1983

[51] Int. Cl.$^4$ ............ G01N 33/50; C07K 15/06; C12P 21/00; C12N 5/00
[52] U.S. Cl. ............ 435/7; 435/29; 435/68; 435/172.2; 435/240; 435/948; 530/387; 935/101; 935/110
[58] Field of Search ............ 435/68, 172.2, 948, 435/240, 7, 29; 424/85; 436/54 B; 260/112, 112 B; 935/89, 99, 101, 106, 110; 530/387

[56] References Cited

U.S. PATENT DOCUMENTS

| | | | |
|---|---|---|---|
| 4,361,550 | 11/1982 | Kung et al. | 424/85 |
| 4,364,932 | 12/1982 | Kung et al. | 424/85 |
| 4,364,933 | 12/1982 | Kung et al. | 424/85 |
| 4,381,292 | 4/1983 | Bieber et al. | 435/172.2 |
| 4,381,295 | 4/1983 | Kung et al. | 424/85 |
| 4,443,427 | 4/1984 | Reinherz et al. | 435/172.2 |

OTHER PUBLICATIONS

Haynes et al., 1979, "Human Lymphocyte Antigens: Production of a Monoclonal Antibody that Defines Functional T-Denied Lymphocyte Subsets", *PNAS*, v76, pp. 5829-5833.

Haynes et al., 1980, "Characterization of a Monoclonal Antibody that Defines an Immunoregulatory T Cell Subset . . . " *PNAS*, v77(5) 2914-18.

Haynes et al., 1981, "Phenotypic Characterization of Cutaneous T-Cell Lymphoma", *N.E.J. Med.*, v304(22), pp. 1319-1323.

Reinherz et al., 1979, "Separation of Functional Human T-Cells by a Monoclonal Antibody", *PNAS*, v76(8), 4061-65.

Evans et al., 1977, "Detection, Isolation, and Functional Characterization of Two Human T-Cell Subclasses . . . , *J. Exp. Med.*, v145, pp. 221-223.

Evans et al., 1978, "Two Functionally Distinct Subpopulations of Human T-Cells that Collaborate in the Generation of Cytotoxic Cells . . . " *J. Imm.*, v120(4), 1423-1428.

Morishima et al., 1982, "Functionally Different T-Lymphocyte Subpopulations Determined by Sensitivity . . . " *J. Imm.*, v129(3) 1091-1098.

*Primary Examiner*—Thomas G. Wiseman
*Assistant Examiner*—Karen Maurey
*Attorney, Agent, or Firm*—John P. White

[57] ABSTRACT

A monoclonal antibody 4A produced by a human-mouse hybridoma cell line is described. In the presence of complement, 4A subsets both cytotoxic and helper T cells creating a diagnostic tool in blood biochemistry.

5 Claims, No Drawings

MONOCLONAL ANTIBODY SUBSETTING HUMAN HELPER AND KILLER T-CELLS AND METHOD

The present invention was wholly or partially made with grants from U.S. National Institutes of Health grants NCI-CA 22507, CA 08748, CA 19267, CA 23766, and Grant NIAID-AI 15227. Therefore, the U.S. government has certain rights in this invention.

The present invention relates to the generation of monoclonal antibodies (mAb) and their use in identifying and characterizing subpopulations of human T-cells.

BACKGROUND

In 1975 Köhler and Milstein introduced a procedure for the production of monoclonal antibodies (mAbs) using hybrid cells (hybridomas) which allows the production of almost unlimited quantities of antibodies of precise and reproducible specificity. Conventional antisera, produced by immunizing animals with tumor cells or other antigens, contain a myriad of different antibodies differing in their specificity and properties, whereas hybridomas produce a single antibody with uniform characteristics. The Köhler-Milstein procedure entails the fusion of spleen cells from an immunized animal with an immortal myeloma cell line. From the fused cells (hybridomas), clones are selected that produce antibody of the desired specificity. Each clone continues to produce only that one antibody. As hybridoma cells can be cultured indefinitely (or stored frozen in liquid nitrogen), a constant supply of antibody is assured.

Antibodies are proteinaceous molecules that have the ability to combine with and recognize other molecules, known as antigens. Monoclonal antibodies are no different from other antibodies except that they are very uniform in their properties and are believed to recognize only one antigen or a portion of an antigen known as a determinant.

In the case of cells, the determinant recognized is an antigen on or in the cell which reacts with the antibody. It is through these cell antigens that a particular antibody recognizes, i.e. reacts with, a particular kind of cell. Thus the cell antigens are markers by which the cell is identified.

These antigenic markers may be used to observe the normal process of cell differentiation and some are sensitive enough to locate differences and abnormalities within a given cell system. The process of differentiation is accompanied by changes in the cell surface antigenic phenotype, and antigens that distinguish cells belonging to distinct differentiation lineages or distinguish cells at different phases in the same differentiation lineage may be observed if the correct antibody is available. Tumor antigens may also be detected. Initial recognition of differentiation antigens came about through analysis of surface antigens of T-cell leukemias of the mouse and the description of the TL, Thy-1, and Lyt series of antigens. (Old, Lloyd J., Cancer Research, 41, 361–375, February 1981) The analysis of these T-cell differentiation antigens was greatly simplified by the availability of normal T cells and B cells of mouse and man. (See U.S. Pat. Nos. 4,361,549–550; 4,364,932–37 and 4,363,799 concerning mAb to Human T-cell antigens).

Progress in defining surface antigens on melanocytes was made possible by the recently discovered technique of culturing melanocytes from normal skin [Eisinger, et al., Proc Nat'l. Acad. Sci. U.S.A., 79 2018 (March 1982), copending patent application Ser. No. 469,854, abandoned.] This method provides a renewable source of proliferating cells for the analysis of melanocyte differentiation antigens.

Cell surface antigens of human malignant melanoma identified by mouse monoclonal antibodies are described as well [Dippold et al. Proc. Nat'l. Acad. Sci. U.S.A. 77, 6114–6118 (1980).] Previous work in human cancer is found in a co-pending patent application Ser. No. 297,814 Monoclonal Antibodies To Cell Surface Antigens of Human Renal Cancer.

The preparation of hybrid cell lines can be successful or not depending on such experimental factors as nature of the innoculant, cell growth conditions, hybridization conditions etc. Thus it is not always possible to predict successful hybridoma preparation of one cell line although success may have been achieved with another cell line. This is due to the difficulty of obtaining a ready source of the appropriate normal cell type as well as the vagaries of the art of monoclonal antibodies.

Functional subpopulations of human T lymphocytes were first demonstrated using heterologous anti-human T cell sera (Evans, R. L., et al. (1977) J. Exp. Med. 145:221; Evans, R. L., et al., (1978) J. Immunol. 120:1423). The introduction of somatic cell hybridization techniques for the production of monoclonal antibodies (mAb) by Köhler and Milstein (Köhler, G., and C. Milstein. (1975) Nature 256:195) has resulted in rapid development of many antibodies for the detection of unique cell surface antigens, selectively expressed on human T lymphocytes and their subpopulations. The human T lymphocyte antigens detected by such antibodies can be divided into at least three groups: (1) pan T cell antigens, which are expressed on virtually all peripheral T cells and/or thymocytes; (2) T cell antigens expressed on inducer/helper T lymphocytes; and (3) antigens expressed on cytotoxic/suppressor T lymphocytes. To date, pan T cell antigens comprise at least three different molecules with m.w. ranges of about 40,000 to 50,000 [e.g., defined by mAb 9.6 (Kamoun, M., et. al. (1981) J. Exp. Med. 153:207, and mAb Leu 5 (Howard, et al. (1981), J. Immunol. 126:2117] 67,000 to 70,000 [e.g., defined by mAb OKT 1 (Kung, P. C., et al. (1979) Science, 206:347; Reinherz, E. L., (1979) J. Immunol. 123:1312); (P. J. Martin, et. al. (1980) Immunogenetics, 11:429), mAb Leu 1 (Wang, C. Y., (1980) J. Exp. Med. 151:1539), mAb T 101 (Royston, I., et al. (1980) J. Immunol. 125:725), and mAb L17F12 (Engleman, E. G., et. al. (1981) Proc. Natl. Acad. Sci. U.S.A. 78:1791); and 20,000 to 30,000 (e.g., defined by mAb OKT 3 (Kung, P. C., Supra mAb Leu 4 (Ledbetter, J. A., et al. (1981) In Monoclonal Antibodies and T Cell Hybridomas. G. J. Hammerling, and J. F. Kearney, eds. Elsevier/North Holland, New York. In press), and mAb 38.1 (Hansen, J. A., and P. J. Martin. (1981) In Workshop on Hybridomas in Cancer Diagnosis and Treatment. M. Mitchell and H. Oettgen, eds. Raven Press, New York. In press). The inducer/helper T lymphocyte subpopulation is defined by mAb OKT 4 (Kung, P. C., et. al. Supra) Reinherz, E. L., et al. (1979) Proc. Natl. Acad. Sci. U.S.A. 76:4061) and mAb Leu 3a (Evans, R. L. et. al. (1981) Thymus-dependent membrane antigens in Proc. Nat. Acad. Sci. U.S.A. 78:544); (Ledbetter, J. A., et al. (1981) J. Exp. Med. 153:310); (Engleman, E. G., et. al. (1981) J. Exp. Med. 153:193). The human T lymphocyte subpopulation containing the cytotoxic/suppressor T cells are defined by other mAb, mAb OKT 5 (Reinherz, et al. (1980) J. Immunol. 124:1301), mAb OKT 8 (Thomas, Y., et. al. (1980) J. Immunol. 125:2402), and mAb Leu 2a (Evans, (1981) Supra, Ledbetter, Supra, Engleman, E. G., J. Exp. Med. Supra). Haynes et al. (Haynes, B. F., et. al. (1979) Proc. Natl. Acad. Sci. U.S.A. 76:5829; Haynes, B. F., et. al. (1980) Proc. Nat. Acad. Sci. U.S.A. 77:2914; Haynes, B. F., et. al. (1981) N. Engl. J. Med. 304:1319; Haynes, B. F. (1981) Immunol. Rev. 57:127) have described a human T lymphocyte specific antigen detected by mAb 3A1. This antibody detects a cell surface antigen with m.w. of 40,000, which is expressed on T helper cells involved in pokeweed mitogen- (PWM) driven in vitro antibody production and on the concanavalin A- (Con A) induced cells that cause in vitro suppression of B cell Ig synthesis.

SUMMARY

We describe here a complement- (C) fixing mAb (mAb 4A) that identifies a human T-cell antigen similar to that of mAb 3A1. The 4A phenotype of functional T lymphocyte suppopulations is best defined on the basis of their sensitivity to mAb 4A+C. Although the 4A antigen is expressed on most peripheral blood T lymphocytes ($81\pm8\%$) [mean$\pm$SD]), there are distinct functional differences in the T cells that can be depleted by C-dependent cytotoxicity (C-cytotoxicity) vs the T cells that are insensitive to antibody +C. The 4A-positive lymphocytes can be divided into sub-populations by their sensitivity to mAb 4A+C. The work of the present invention is described in a published paper Morishima et al., J. Immunology, 129 1091 (Sept. 1, 1982) which is hereby incorporated by reference.

DESCRIPTION

The following description of methods used is for illustrative purposes only. Equivalent processes can yield similar results.

Cell preparation. Heparinized blood from healthy adult donors was drawn, and the peripheral blood mononuclear leukocytes (PBL) were isolated by Ficoll-Hypaque density gradient centrifugation (Lymphoprep, Accurate Chemical Co., Hicksville, N.Y.) (Boyum, A. (1968) Scad. J. Clin. Lab. Invest. 97:21s). Adherent mononuclear cells (monocytes) were obtained by incubating PBL ($1 \times 10^7$ in 5 ml of RPMI 1640 [GIBCO, New York, N.Y.]) with 10% fetal calf serum (FCS) in $60 \times 15$ mm tissue culture dishes (Falcon Plates, Oxnard, Calif.) for 60 min at 37° C. After the nonadherent cells were collected by washing the dishes with RPMI 1640, the adherent cells were detached by further incubation with phosphate-buffered saline (PBS) containing 0.2% EDTA and 1% FCS. More than 80% of adherent cells had the morphologic characteristics of monocytes. T cell-enriched cell populations were prepared by passing a nonadherent PBL suspension over a nylon wool column (Leuko-Pak leukocyte filter, Fenwall Labs, Travenol, Ill.) as described by Danilovs et al. (Danilovs, J. A., et. al. (1980) In Histocompatibility Testing 1980. P. I. Terasaki, ed. U.C.L.A. Tissue Typing Laboratory, California. P. 287). Fifteen to $20 \times 10^6$ cells in 0.4 ml of RPMI 1640 with 10% FCS were applied to the nylon wool column and incubated for 45 min at 37° C. After incubation, the T cell-enriched fraction was eluted with 10 ml of RPMI 1640 with 10% FCS. The non-T cell-enriched cell fraction was collected by squeezing the column with a plunger. The T cell-enriched population contained more than 95% sheep red blood cell (SRBC) rosetting cells, and the non-T cell-enriched population contained more than 80% of surface Ig-positive cells (Ig=Immunoglobulin), which were determined by direct immunofluorescence (IF) using fluorescence (FITC) conjugated F(ab')$_2$ fragment of goat anti-human Ig (Cappel Labs, Cochranville, Pa.). Polymorphonuclear cells (granuloctyes) were recovered from the buffy coat of the lower layer in the Ficoll-Hypaque gradient centrifugation of heparinized blood. The red blood cells were removed through the process of sedimentation using 6% dextran sulfate in saline (Abbott Labs, Chicago, Ill.). More than 95% of the cells had the morphologic characteristics of granulocytes. The platelets were collected from the interface after Ficoll-Hypaque gradient centrifugation of heparinized blood. This fraction was resuspended in PBS and centrifuged for 10 min at $200 \times G$, and the platelet-rich supernatant was recovered.

Phytohemagglutinin- (PHA) transformed T cells and Con A transformed T cells were obtained after in vitro lymphocyte transformation: the T cell-enriched cell populations were incubated at a concentration of $0.5 \times 10^6$ cells/ml in complete medium (RPMI 1640 with 10% pooled human serum [Bio-Bee, Inc., Boston, Mass.] supplemented with 100 U penicillin, 100 microgram streptomycin, and 2 mM L-glutamine/ml), and PHA-16 (1.25 microgram/ml) (Wellcome Reagent, Kent, England) or Con A (25.0 microgram/ml) (Pharmacia, Piscataway, N.J.) at 37° C. in a humidified incubator with 5% $CO_2$ for 4 days. Human spleen B cells were activated by rabbit antiserum specific to B cell antigen GP54 prepared by C. Y. Wang (Wang, C. Y., et. al. (1979) J. Exp. Med. 149:1424).

The following histologically normal tissues were prepared by mincing the tissues and filtering the resulting cell suspension through a mesh. Thymocytes were obtained from the thymuses of children who were undergoing cardiac surgery. Spleen cells were prepared from the spleens obtained during abdominal surgery. Bone marrow mononuclear cells were isolated from the interface after Ficoll-Hypaque density gradient centrifugation.

Leukemia cells were provided from the haematology laboratory of Nagoya University. The samples contained more than 90% of leukemia cells obtained from nontreated leukemia patients' peripheral blood or bone marrow, and stored at 180° C. in liquid nitrogen.

Tumor cell lines established in vitro from nonhemopoietic tissues were obtained from the cell library of Dr. L. Old, Sloan-Kettering Institute for Cancer Research (S.K.I.). The cell lines used were as follows: brain tumors BZ and AJ; renal tumors SK-RC-7 and SK-RC-18; melanomas SK-mel-29 and SK-mel-37; bladder tumors T-24 and J-82; osteosarcoma U-20S; lung tumor SK-LC-LL; uterine tumor ME-180; liver cancer SK-HEP-1; and colon tumor SW-1221. The hematopoietic cell lines were obtained locally or from other investigators. The following B lymphoblastoid cell lines (B cell lines) were used: DAUDI from Dr. G. Klein, Stockholm; WALK and PB from S.K.I.; SB from the American Type Culture Collection (ATCC). The T lymphoid cell lines (T cell lines) used were as follows: HSB-2 and CCRF-CEM from ATCC; MOLT-4 and RPMI 8042 from Dr. J. Minowada, Roswell Park Memorial Institute; and 45 from Dr. P. Ralph, S.K.I. The monocytic cell line U-937 was obtained from Dr. P. Ralph, S.K.I. The erythroleukemia cell line K-562 was obtained from Dr. G. Klein, Stockholm. All cell lines were maintained in culture medium containing RPMI 1640 supplemented with 10% FCS, 100 U penicillin, 100 microgram streptomycin, and 2 mM L-glutamine/ml. T and B cell lines were tested at regular intervals for the presence of the appropriate T or B cell markers. HLA typing of the cell lines were used to exclude cross-contamination of cell lines as described by Hansen. (Hansen, J. A., et. al. (1979) Immunogenetics 8:51) and Pollak (Pollack, M. S., et. al. (1980) Tissue Antigens 15:249).

Example of Production of mAb. According to the hybridoma procedure by Köhler and Milstein, Supra, BALB/c mice were immunized i.p. three times every 2 wk with $1 \times 10^7$ PHA-transformed human T lymphocytes. On the third day after the last immunization, $2.2 \times 10^8$ of immunized spleen cells were fused with $4.4 \times 10^7$ of murine myeloma culture cells (NS-1) with a 40% solution of polyethylene glycol 4000 (Sigma, St. Louis, Mo.). The fused cells were cultured in RPMI 1640 supplemented with 15% FCS, hypoxanthine, aminopterin, and thymidine in flat-bottom microculture plates (Cat. No. 3596, Costar, Cambridge, Mass.). In order to detect hybridoma clones that produce antibodies to immunized cells, the supernatant of each culture well was tested by the standard two-stage NIH C-dependent microcytotoxicity method (Mittal, K. K., (1978) Transplantation 25:275). After two successive limiting dilutions, the hybridoma clone designated as 4A was established. The supernatant of 4A hybridoma culture was harvested. Ascites containing mAb 4A was produced by the infection of 4A hybridoma clone cells into BALB/c mice i.p.. MAb 4A was purified by protein A-Sepharose column chromatography (Ey, P. L., et. al. (1978), Immunochemistry 15:429), and the F(ab')$_2$ fragment of purified mAb 4A was prepared by the method of Coding (Coding, J. W. (1976) Immunol. Methods, 13:215.

MAb 3A1 was kindly provided by Dr. Haynes. MAbB NL-1, which detects an antigen similar to the common ALL antigen, was kindly provided by Dr. Ueda (Ueda. R., et. al. Proc. Natl. Acad. Sci. U.S.A. in press), and Mab 6A1, which detects the common antigenic determinant of human DR antigen (m.w. 33,000 and 28,000), was produced by us.

Indirect IF. The indirect IF was performed with saturating concentrations of mAb 4A supernatant and the F(ab')$_2$ fragment of purified antibody. $2 \times 10^6$ cells were incubated with 0.05 ml of mAb 4A (1:20 dilution of supernatant or 1:100 dilution of F(ab')$_2$ fragment of purified mAb 4A) at 4° C. for 30 min. Excess antibody was removed by washing twice in PBS containing 0.4% bovine serum albumin and 0.02% sodium azide (PBS-NaN$_3$) for 30 min, then 0.05 ml FITC-conjugated goat anti-mouse IgG (1:10 dilution) (Litton Bionetics, Kensington, Md.) was added, and the mixture was incubated for another 30 min at 4° C. The cells were further washed in PBS-NaN$_3$, and the percentage of fluorescence-positive cells was counted using a phase-contrast fluorescent microscope (Leitz, West Germany). Selected samples were also analyzed using a fluorescence-activated cell sorter (FACS IV; Becton Dickinson, Mountain View, Calif.). Twenty-five thousand cells per sample were counted in two different conditions, Power 200 mw, PMT 532 V and Power 500 mw, PMT 700 V. Intensity of IF was marked in linear scale.

In some experiments, direct IF was employed using FITC-conjugated mAb Leu-1, mAb Leu-2a, and mAb Leu-3a (Becton Dickinson). $2 \times 10^6$ cells were incubated with 0.05 ml of FITC-conjugated mAb (1:10 dilution) at 4° C. for 30 min.

Quantitative C-cytotoxicity assay. $1 \times 10^7$ of PBL or T cells were incubated with 1 ml of mAb 4A (1:20 dilution of supernatant) at 4° C. for 30 min. Excess mAb was removed by washing cells once in RPMI 1640, and 1 ml of prescreened rabbit C (Pel-Freez, Rogers, Ar) (1:2 dilution) was added. After the incubation for 60 min at 37° C., the percentage of dead cells was counted by the trypan blue dye exclusion method. The dead cells were removed by the Ficoll-Hypaque density gradient centrifugation, and the recovered cells were used for some experiments after washing cells two times in RPMI 1640.

Absorption test. In vitro cultured cell lines of hematopoietic and nonhematopoietic origin were mechanically detached from the culture flask and then washed twice in PBS before the absorption. A volume of 0.05 ml packed cells was suspended in a 1:1 ratio of mAb 4A (1:20 dilution of supernatant) and incubated for 1 hr at 4° C. The remaining activity of absorbed mAb 4A was then tested by the standard two-stage NIH microcytotoxicity method (Mittal, Supra) with T cells used as target cells.

Determination of Ig subclass of mAb 4A. MAb 4A (culture supernatant) was concentrated five times, and its Ig subclass and concentration were determined by the double immunodiffusion method (Ouchterlony, O. (1958). In Progress in Allergy, Vol. V., P. Kallos, ed. Karger, Basel. P.1.) using goat or rabbit antisera to mouse IgM, IgG1, IgG2b, and IgG3 (Litton Bionetics), and the Ig concentration of 4A supernatant was measured by the single radical immunodiffusion method (Mancini, et. al. (1965), Immunochemistry 2:235) with goat anti-serum to mouse IgG2A and purified IgG2A (Litton Bionetics) used as a standard.

Determination of m.w. Lymphoid cells were metabolically labeled in the presence of [$^3$H]-glucosamine or [$^{35}$S]-methionine. For the preparation of [$^3$H]-glucosamine-labeled cells, about $5 \times 10^7$ cells were grown at 37° C. for 40 hr in 10 ml of Eagle's minimal essential medium supplemented with 10% FCS, 1% (w/v) nonessential amino acids, 2 mM 1-glutamine, 100 U penicillin, 100 microgram streptomycin/ml, and 150 microCi of [$^3$H]-glucosamine (19.0 Ci/mM, New England Nuclear, Boston, Mass.). For the preparation of [$^{35}$S]-methionine-labeled cells, $6 \times 10^7$ cells were washed in methionine-free RPMI culture medium, then resuspended in 4 ml of the same medium with 200 microCi of [$^{35}$S]-methionine (995.38 Ci/mM; New England Nuclear). This mixture was cultured for 16 hr. The labeled cells were washed twice with Dulbecco's PBS and extracted with 1% (v/v) Nonidet P-40 (NP-40) (Sigma Chemical Co., St. Louis, Mo. chemical name octylphenoxypolyethoxyethanol) in 0.02M Tris-HCl buffer (pH 7.5) containing 0.3% sucrose, 3 mM MgCl$_2$, and 1 mM phenylmethylsulfonyl fluoride for 60 min at 4° C. Insoluble material was removed by centrifugation at 1500×G for 15 min. The supernatant was diluted with an equal volume of the same buffer without NP-40 and filtered through a 0.22-micrometer filter (Millipore, Bedford, Mass.). Five microliters of mAb ascites were added to the NP-40 extracts of [$^3$H]-glucosamine-labeled cells. The reaction mixture was then incubated at 4° C. for 16 hr before 100 microliters of a 10% suspension of *Staphylococcus aureus* (Bethesda Research Laboratories, Gaithersburg, Md.) were added to isolate immune complexes. The precipitated material was analyzed by 10% SDS-polyacrylamide gel electrophoresis (SDS-PAGE) as previously described (Ogata, R., et. al. (1981) Proc. Natl. Acad. Sci. 78:770).

In vitro antibody production to SRBC and to the 2, 4, 6-trinitrophenyl groups (TNP). The detailed methods were described by M. Hoffmann previously (Hoffmann, M. K. 1980. Proc. Natl. Acad. Sci. U.S.A. 77:1139). Briefly, PBL were suspended in complete Mishell-Dutton culture medium containing, in addition, 2-mercaptoethanol ($5 \times 10^{-5}$M). One-tenth milliliter of PBL at concentrations ranging from 1 to $5 \times 10^6$/ml (unless stated otherwise) was placed in flat-bottom microculture plates and immunized with SRBC (0.03% final concentration) or TNP-conjugated burro red blood cells (BRBC). Cultures also received monocyte-conditioned medium (10%) as sources of interleukin 1 (IL 1) and heat-inactivated S. aureus (0.03% final concentration). A human serum pooled from blood type AB donors was added to a final concentration of 10%, 20 to 24 hr later. Cultures were fed daily with 10 microliters of a nutritional cocktail and were harvested on day 6. Antibody-forming cells were determined by hemolytic plaque assays, and were expressed as plaque-forming cells (PFC) per $1 \times 10^6$ T cells and non-T cells that were separated by the SRBC rosetting method (Weiner, M. S., et. al. (1973) Blood 42:939) with neuraminidase-treated SRBC were used in some experiments.

Lymphocyte transformation in vitro to mitogens. $5 \times 10^4$ PBL in complete medium were incubated in a round-bottom microculture plate (Cat. No. 1482 Vanguard International, Neptune, N.J.). The lymphocytes were stimulated with PHA-P (Difco, Detroit, Mich.), 8.25 microgram/culture; Con A (Pharmacia), 5.0 microgram/culture; and PWM (GIBCO), 0.5 microgram/culture. All cultures were performed in triplicate and cultured at 37° C. in a humidified atmosphere containing 5% $CO_2$. PHA- and Con A-stimulated cultures were incubated for 37 hr and labeled with 0.02 Ci/culture of $^{14}$C-thymidine ($^{14}$C-TdR), specific activity 0.23 mCi/mg (New England Nuclear) for the last 16 hr of culture. The PWM-stimulated cultures were incubated for 96 hr and then labeled for 16 hr. The $^{14}$C-TdR incorporation was measured by liquid scintillation counting (Cunningham-Rundles, S., et. al. (1976), In clinical Immunobiology, Vol III. Academic Press, New York. P. 151).

Mixed lymphocyte cultures (MLC). One-way MLC from unrelated HLA-D-imcompatible PBL donors were performed. Various numbers of responder PBL and $5 \times 10^4$ irradiated (2000 rad) PBL in 200 microliters of complete medium in round-bottom microculture plates were incubated at 37° C. in 5% $CO_2$ atmosphere. One microcurie of $^3$H-TdR, specific activity 6.7 Ci/mM (New England Nuclear), per culture well was added after 120 hr in culture. After an additional 16 hr, the cells were assayed for incorporated label by liquid scintillation counting (Hansen, J. A., et. al. (1977) Transplantation 23:366).

Generation of cytotoxic lymphocytes. $10 \times 10^6$ of both responder PBL and stimulating PBL were co-cultured in a tissue culture flask (25 cm$^2$, Falcon, Cockeyesville, Md.) in 20 ml of complete medium as described by Schendel et al. (Schendel, D. J., et. al. (1978). Eur. J. Immunol. 8:634). Simulator cells were inactivated with 2000 rad of X-irradiation. The upright flask was incubated for 6 days at 37° C. in a humidified incubation with 5% $CO_2$. After 6 days, the cells from several flasks were pooled and used as effector cells in the cell-mediated lympholysis (CML) assay.

CML assay. The CML assay was performed by the method described by Schendel et al. Supra. Target cells were prepared 72 hr before CML assay. $10 \times 10^6$ PBL were cultured in 10 ml of complete medium containing PHA at a 1:100 dilution of stock solution (PHA-M; Difco). On the day of the CML assay, the cells were transferred to a plastic tube, spun at $150 \times G$ for 8 min, and resuspended in approximately 0.2 ml of the supernatant medium. Then, 250 microCi of $^{51}$Cr sodium chromate, specific activity 200 to 500 mCi/mgCr (New England Nuclear), per tube were added, and the mixture was incubated for 1 hr. The cells were than washed three times and suspended at a concentration of $3 \times 10^4$/ml in complete medium.

The cytoxic assays were performed in round-bottom microculture plates. Each well contained 100 microliter of target cell suspension (3000 cells/well) and 100 microliter of the effector cell suspension. The effector:target cell ratios were 100:1, 50:1, and 25:1. After incubation for 4 hr at 37° C., radioactive supernatants were collected by the Titertek harvesting system (Flo Labs, Rockville, Md.) and counted for 1 min in a gamma counter (model 1185, Nuclear Chicago, Chicago, Ill.). Spontaneous release (SR) was determined by incubation of the target cell alone. Maximum release (MR) was determined by exposing the target cells to 100 microliters of 5% Triton X-100 (New England Nuclear). Percentage of cytoxicity was calculated by the formula:

$$\% \ CML = \frac{\text{Experimental release} - SR}{MR - SR} \times 100$$

EXAMPLE I

Example of m.w. and Ig subclass determination for mAb 4A. Immunoprecipitates of [$^3$H]-glucosamine-labeled extracts of the T cell line CCRF-CEM were analyzed by sodium dodecyl sulfate-polyacrylamide gel electrophoresis (SDS-PAGE). MAb 4A precipitated one band of glycoprotein of about 40,000 daltons in reduced conditions. (See FIG. 1 Morishima, Supra). When another T cell line, HSB-2, was labeled with [$^{32}$S]-methionine, mAb 4A precipitated the same band in reduced and nonreduced conditions. Sequential immunoprecipitation with mAb 4A and mAb 3A 1 was done using [$^{32}$S]-methionine-labeled lysate of CCRF-CEM. One part of the lysate was reacted with staphylococcyl protein A precoated with 20 microgram of mAb 4A, and the other was precoated with 20 microgram of mAb 3A 1 for 30 min at 4° C. Immunoprecipitation was repeated with the same mAb two more times. The precleared lysate was subjected to the second mAb 3A 1 or 4A as the same procedure described in the method. Only the first immonoprecipitation of both cell lysates showed 40,000 m.w. bands. This finding may indicate that mAb 4A and mAb 3A 1 detect the same or a similar molecule. mAb 4A and 3A1 may also detect determinants near each other on the cell surface or some combination of the above. The Ig subclass of mAb 4A was IgG2A, K, and the supernatant of 4A hybridoma contained 0.06 mg/ml of IgG2a.

EXAMPLE II

Example of tissue distribution of 4A antigen. MAb 4A reacted with the majority of peripheral T cells. The data are summarized in Table 1 below. By indirect IF, 81±8% (n=22) of PBL T cells reacted with mAb 4A. When the intensity of fluorescence was analyzed by FACS IV, there were wide variations of the intensity among T cells, from weakly positive to moderately positive ones (See FIG. 2 Morishima, Supra). MAb 4A also reacted with 90% of thymocytes, 49% of spleen mononuclear cells, and 5% of bone marrow cells. A small percentage (1 to 5%) of cells in the non-T cell fraction of PBL and in the monocyte fraction were positive when the F(ab')$_2$ fragment of purified MAb 4A was used. This positive result might be partially due to the contamination of T cells; however, the possibility still remained that very few (on the order of 1 to 5%) of the non-T cell population of lymphocytes and monocytes could be 4A antigen positive. Four T cell lines were found to be positive, and one T cell line, MOLT 4, was only weakly positive. All B cell lines tested, one erythroleukemia cell line (K-562), and the monocytic cell line U937 were negative.

TABLE 1

Examples of 4A antigen expression on various human hematopoietic cells

| Cells | Positive %[a] |
|---|---|
| T lymphocyte (22)[b] | 81 ± 8 |
| Non-T lumphocyte | (see footnote[c]) |
| Monocyte | (see footnote[c]) |
| Granulocyte (11) | 0 |
| Red blood cell (10) | 0 |
| Platelet (10) | 0 |
| Thymocyte (3) | 90 ± 4 |
| Splenocyte (3) | 49 ± 3 |
| Bone marrow cell (2) | 5 ± 1 |
| T cell line | |
| HSB-2 | positive |
| CCRF-CEM | positive |
| 45 | positive |
| 8402 | positive |
| MOLT-4 | weakly positive |
| B cell line | |
| SB | negative |
| WALK | negative |
| PB | negative |
| DAUDI | negative |
| Erythroleukemia cell line K562 | negative |
| Monocytic cell line U937 | negative |

[a]Percentage of indirect immunofluorescent positive cells (mean ± SD).
[b]Number of tested samples.
[c]When F(ab')$_2$ fragment of purified mAb 4A was used, non-T lymphocyte (n = 4)3 ± 1% was positive and monocyte was (n = 4) 4 ± 1% positive, whereas supernatant of mAb 4A showed non-T lymphocyte (n = 12) to be 8 ± 3% weakly positive, and monocyte (n = 10) to be 35 ± 12% weakly positive.

The expression of 4A antigen on various kinds of leukemia cells was tested by the C-dependent micrototoxicity test (Mittal, K. K., et al. Supra) (Table II below). 4A antigen-positive leukemia cells were restricted to SRBC rosette-positive acute lymphoblastic leukemia (T-ALL) and SRBC rosette-negative, DR-negative ALL. In contrast to this, the SRBC rosette-negative DR-positive ALL, adult T cell leukemia (ATL), which occurs in southern Japan (Uchiyama, T., et. al. (1977) Blood 50:481), Sezary leukemia, B cell-type chronic lymphocytic leukemia (B-CLL), acute myeloblastic leukemia (AML), acute myelomonocytic leukemia (AMMOL), and acute monocytic leukemia (AMOL) expressed no 4A antigen on the surface of leukemia cells.

The cytotoxic activity of mAb 4A supernatant used in 1:20 dilution could be completely removed by the T lymphoblastoid cell line CCRF-CEM after incubation with supernatant:packed cell volume 10:1. The absorption studies using nonhematopoietic tumor cell lines were therefore performed with equal volumes of packed cultured cell lines and mAb 4A supernatant. The following cell lines were used: BZ and AJ (brain cancer), SK-RC-7 and SK-RC-18 (renal cancer), SK-MEL-29 and SK-MEL-37 (melanoma), T-24 and J-82 (bladder cancer), U-20 S (Osterosarcoma), SK-LC-LL (lung cancer), SK-HEP-1 (liver cancer), and SW-1221 (colon cancer). None of these cell lines removed the antibody.

TABLE II

Example of 4A antigen expression on various human leukemia cells

| Cells | No. of Case | E[a] | S-lg[b] | DR[c] | CALLA[d] | MAb 4A[e] |
|---|---|---|---|---|---|---|
| ALL (T cell) | 6 | + | − | − | − | + |
| ALL | 4 | − | − | − | − | + |
| ALL (null cell) | 12 | − | − | + | +/− | − |
| ATL[f] | 5 | + | − | − | − | − |
| Sezary | 2 | + | ND[g] | + | ND | − |
| B-CLL | 5 | − | + | + | ND | − |
| AML | 4 | − | ND | +/− | ND | − |
| AMMOL | 3 | − | ND | +/− | ND | − |
| AMOL | 3 | − | ND | − | ND | − |

[a]SRBC rosetting test; +: more than 20% −: less than 5%.
[b]Tested by direct immunofluorescence using FITC-conjugated goat anti-human Ig.
[c]Tested by cytotoxicity test using mAb 6A 1 ascites; +: more than 95% positive with more than or equal to 5000 times dilution of ascites.
[d]Tested by cytotoxicity using mAb NL-1 supernatant, which detects an antigen similar to common ALL antigen (CALLA); +: more than 95% positive with more than or equal to 10 times dilution of supernatant.
[e]Tested by cytotoxicity test using mAb 4A ascites; +: more than 95% positive with more than or equal to 30,000 times dilution of ascites f) Adult T cell leukemia (41).
[g]Not done.

EXAMPLE III

Example of the expression of T cell antigen before and after the treatment with mAb 4A+C. Although IF demonstrated the 4A antigen on 81% of peripheral T cells, in the quantitative C-cytotoxicity assay, the treatment with mAb 4A+C-cytotoxicity assay, the treatment with mAb 4A+C resulted in 46±6% (mean±SD) (n=12) cytotoxicity of unseparated PBL and 57±6% (n=6) cytotoxicity of PBL T cells. After the removal of killed T cells by the Ficoll-Hypaque density gradient separation, the expression of 4A antigen on recovered viable T cells was tested by IF using FACS IV. The cytofluorographic data demonstrated clearly that the T cells that had been removed by treatment with mAb 4A+C had a higher intensity of fluorescence (4A++) than the recovered viable T cells. In other words, the T cells that express 4A antigen weakly (4A+) were not killed by C-cytotoxicity assay. The possibility that the antigenic modulation of 4A antigen after the incubation with C at 37° C. was excluded, because the intensity of cytofluorograph of 4A antigen after the incubation with mAb 4A at 37° C. for 1.5 hr was the same as the intensity after incubation at 4° C. for 1.5 hr.

The changes of T cell subsets before and after treatment with mAb 4A+C were tested by direct IF, using mAb Leu 1, mAb Leu 2a, and mAb Leu 3a, which were directly conjugated with FITC (Table III below).

TABLE III

Example of T Lymphocyte phenotype in PBL-T cells and 4A T cells[a]

| | Untreated T Lymphocytes PBL-T Cells[b] | | | | | MAb + C-treated T Lymphocytes 4A T Cells[b] | | | | |
|---|---|---|---|---|---|---|---|---|---|---|
| MAb | I | II | III | IV | X ± SD | I | II | III | IV | X ± SD |
| 4A | 86[c] | 77 | 85 | —[d] | 83 ± 4.9 | 10 | 16 | 13 | — | 13 ± 2.1 |

TABLE III-continued

Example of T Lymphocyte phenotype in
PBL-T cells and 4A T cells[a]

| MAb | Untreated T Lymphocytes PBL-T Cells[b] | | | | | MAb + C-treated T Lymphocytes 4A T Cells[b] | | | | |
|---|---|---|---|---|---|---|---|---|---|---|
| | I | II | III | IV | X ± SD | I | II | III | IV | X ± SD |
| Leu 1 | 91 | 86 | 80 | 80 | 84 ± 5.3 | 96 | 84 | 78 | 79 | 84 ± 8.3 |
| Leu 2a | 33 | 36 | 45 | 27 | 38 ± 6.2 | 36 | 29 | 38 | 28 | 33 ± 5.0 |
| Leu 3a | 59 | 43 | 58 | 44 | 51 ± 8.7 | 66 | 63 | 52 | 49 | 59 ± 8.3 |

[a]T Lymphocyte phenotypes were determined by MAb Leu 1, mAb Leu 2a, mAb Leu 3a, and mAb 4A before and after treatment with mAb 4A and C. The 4A-positive T cells were determined by indirect IF. The percentages of Leu 1-, Leu 2a-, and Leu 3a-positive cells were determined by direct IF with FITC-conjugated antibodies.
[b]I, II, III, and IV denote four different T cell donors. X ± SD denotes mean value ± SD. Treatment with mAb 4A + C removed 55 ± 4.6% of the T cells.
[c]Percentage of IF-positive cells.
[d]—, Not done.

The remaining viable cells after the treatment of mAb 4A+C were found to contain the same relative proportions of Leu 1-positive cells, Leu 2a-positive cells, and Leu 3a-positive cells as were found in the untreated PBL-T cells. The percentage of 4A-positive cells as determined by IF, whoever, was decreased from 83% to 13%. These results indicate that mAb 4A recognizes different sets of T cell subpopulations from the ones defined by mAb Leu 1, mAb Leu 2a, and mAb Leu 3a.

The following experiments were performed in order to determine the functional properties of 4A high-density cells (4A++) (i.e., sensitive to mAb 4A+C) and 4A low-density cells (4A+)(i.e., not sensitive to mAb 4A + C). These two lymphocyte subsets were investigated by comparing the results obtained using unseparated, untreated PBL or purified untreated peripheral T cells with the experiments using mAb 4A+C-treated PBL or T cells as described above (quantitative C-cytotoxicity assay).

EXAMPLE IV

Example of expression of 4A antigen and in vitro lymphocyte transformation. PBL were tested for their capacity to undergo in vitro transformation in response to mitogens (i.e., PHA, Con A, and PWM) and to allogeneic cells (MLC) before and after treatment with mAb 4A+C. The data presented in Table III demonstrate that the removal of the 4A cells resulted in the moderate reduction of mitogen response. In contrast to this, it was found that the treatment of responder cells with mAb 4A+C did not decrease the allogeneic in vitro response (Table IV).

Several experiments were performed in order to establish the lack of effect of mAb 4A+C on responder cell proliferation in MLC.

TABLE IV

Example of Effect of treatment with mAb 4A + C on in vitro lymphocyte transformation (a)

| Stimulation | Untreated PBL | Ab-Treated PBL | % Change (untreated - treated) |
|---|---|---|---|
| PHA stimulation (3 days) | 11,723[b] (44)[c] | 7,274 (38) | −37% |
| Con A stimulation (3 days) | 7,366 (44) | 4,680 (38) | −36% |
| PWM stimulation (4 days) | 7,097 (69) | 5,370 (113) | −24% |
| Allogenic MLC[c] | | | |
| A.Ax (3 days) | 286[e] | — | +14% |
| A.Bx | 842 | 960 | |
| A.Ax (6 days) | 1,030 | — | −9% |
| A.Bx | 16,538 | 15,001 | |
| A.Ax (9 days) | 1,013 | — | +12% |
| A.Bx | 23,965 | 26,746 | |
| A.Ax (12 days) | 918 | — | −23% |
| A.Bx | 5,295 | 4,050 | |

[a]PBL were treated with mAb 4A + C before initiation of in vitro culture. The mitogen-activated cells were cultured for 3 to 4 days, and the blast transformation induced by PHA, Con A, and PWM was determined by [14]C-TdR incorporation during the last 16 hr of culture. The effect of mAb 4A + C on responder lymphocytes was determined by pretreatment of responder PBL (A) with mAb 4A + C. The MLC were performed using X-irradiated (2000 rad) inactivated simulator cells (B). Quantitation of lymphocyte activation was determined after 3, 6, 9, and 12 days of in vitro culture by labelling with [3]H-TdR during the last 16 hr of incubation. Mitogen stimulation and allogeneic MLC were performed with 5 × 10[4] untreated PBL, whereas the mAb 4A + C-treated cells were adjusted to the same volume as the untreated cell suspensions. Treatment of mAb 4A + C resulted in the removal of 47 to 48% of PBL.
[b]cpm of [14]C = TdR incorporation.
[c]Numbers in parentheses are cpm in corresponding unstimulated cells.
[d]Allogeneic MLC; A denotes responder cells, Bx denotes X-irradiated (2000 rad) stimulating cells, A.Ax denotes autologous cell mixture.
[e]cpm of [3]H-TdR incorporation.

The data in FIG. 3 Morishima, Supra demonstrate that when the cell concentration in the antibody-treated sample was not adjusted (i.e., the antibody-treated sample was adjusted to the same volume as the untreated sample), no effect was found for the MLC response in the concentration range of responder cells from 2.5 to 10×10[4] cells/culture. When the cell concentration of the responder cell in mAb 4 A+C-treated sample was adjusted to the same concentration as in the untreated sample, the proliferative response was increased.

The change of the 4A antigen expression after the in vitro response to mitogens was studied using the FACS IV. The effect of simulation with PHA and Con A on the expression of 4A antigen density is shown in FIG. 4 (a–f) Morishima, Supra. Untreated PBL (FIG. 4a) were stimulated with PHA (FIG. 4c) and Con A (FIG. 4e). It was observed that the fluoresence intensity was increased after 4 days of in vitro culture. The T cells obtained after in vitro treatment with mAb 4A+C demonstrated that the remaining T cells had low density of the 4A antigen (4A+) (FIG. 4b). When the 4A+ T cells were stimulated with PHA (FIG. 4d) or Con A (FIG. 4f), they were found to have strongly increased expression of the 4A antigen. The cytofluorograms obtained after 4 days of in vitro culture were not significantly different for the untreated T cells as compared with the cytofluorograms obtained for mAb 4A-treated T cells. These data demonstrated that 4A+ T cells after in vitro activation with mitogens became 4A++ T cells. It can be seen in the above mentioned FIG. 4 of Morishima that some of the activated T cells had greatly increased expression of the 4A antigen, and that some cells had 4A antigen density that far exceeded the highest 4A antigen expression found in peripheral blood T cells.

Studies of the tissue distribution of the 4A antigen had shown that this antigen was not present on B lymphoblastoid cell lines, cells from patients with B-CLL, or on peripheral blood B lymphocytes. It was possible, however, that this antigen would be expressed on in vitro activated B lymphocytes. It has been shown that the heterologous rabbit antiserum anti-GP54 exclusively activated human B lymphocytes (Wang, C. Y., et. al. (1979) J. Exp. Med. 149:1424). B lymphocytes were isolated from spleen samples, and these B cells were stimulated with rabbit anti-GP54. Unstimulated and anti-GP54 antibody-stimulated B cells were studies in the FSCS IV for expression of 4A. As shown in FIG. 5 Morishima, Supra, there was no increase in 4A antigen expression after B cell activation.

EXAMPLE V

The effects of mAb 4A+C on the helper functions that induce the antibody production of B cells specific to SRBC and TNP. The involvement of 4A++ cells in this reaction was tested by cytolytic treatment of either unseparated PBL cell suspensions or by treating isolated T cells (SRBC rosette-positive cells). Treated T cells were co-cultured with B cells and immunized in culture with SRBC and BRBC-TNP. PFC were assayed on day 6 (FIGS. 6A and 6B Morishima, Supra). Helper T cell activity was found to be abrogated by treatment of T cells with mAb 4A+C. PFC responses were also abrogated by treating whole PBL cell suspensions with mAb 4A+C (FIGS. 6C, 6D Morishima, Supra). These results show that 4A is expressed on helper T cells involved in this response and imply that this helper cell population belongs to the fraction of high-density 4A T cells (4A++).

EXAMPLE VI

Example of expression of 4A antigen on cyctotoxic, alloreactive T lymphocytes. Because it was shown that treatment with mAb 4A+C had no effect on cell proliferation in vitro in MLC, it was of interest to study whether this treatment had any effect on the generation of alloreactive, cytotoxic T cells. The cytotoxic T cell response was therefore studied after 6 days in vitro MLC using the standard CML assay. Results obtained in the untreated MLC were compared with the results obtained in the MLC in which the responder PBL had been treated with mAb 4A+C before the initiation of culture.

As shown in FIG. 7A (Morishima, Supra,) there was no effect on the generation of alloreactive, cytotoxic T cells when the responder cells had been pretreated with mAb 4A+C. The same degree of cytotoxicity was obtained as in the untreated cell combinations. This figure also demonstrated that the same level of cytotoxicity was obtained when the treated responder PBL in MLC were adjusted or unadjusted in cell number before the initiation of the MLC. These experiments indicate that the precursor T cells in peripheral blood that respond to alloantigens are present in the 4A+ cell population, and that the alloreactive cytotoxic T cell precursors are also present in 4A+ cells.

Although the precursor cells for the alloreactive, cytotoxic T cells in PBL were determined to be 4A+ cells, it was found that 4A antigen was expressed on the cytotoxic T cells. This was established by treating day 6 MLC combinations with mAb 4A+C before the cytotoxicity test and comparing the results with the results obtained in the untreated cell mixture (FIG. 7B Morishima, Supra). These studies demonstrated that the cytotoxic T cell was completely removed by the treatment with mAb 4A+C. Also in this instance, there was no effect of adjusting the cell concentration to the same concentration as in the untreated cell mixture.

Thus, specific antigenic response to 4A is further defined by mAb 4A plus complement which occurs with different quantitative levels, i.e. differing reaction ranges from strong to weak on functional subsets of peripheral T-lymphocytes. The antigen is a glycoprotein with a relative m.w. of approximately 40,000 (determined under reducing and nonreducing conditions). The 4A antigen is expressed on almost 80% of peripheral T cells, and the amount of 4A antigen among positive cells varies in reaction from strong to weak. It is noteworthy to point out that this 4A mAb can distinguish the E rosette-positive ALL and E rosette-negative, DR-negative ALL from more mature T cell leukemia (i.e., ATL and Sezary cells), E rosette-negative, DR-positive ALL AML, AMMOL, and AMOL.

The present invention demonstrates that the functional characteristics of peripheral T cells with the 4A phenotype is correlated with the expression of this antigen as determined by the sensitivity of the T cells to C-mediated cell lysis. The 4A-positive T lymphocytes can be divided into two populations by their sensitivity to mAb 4A+C: 4A high-density T cells, strongly reactive, (4A++), which are killed in vitro by the antibody in the presence of C, and 4A low-density T cells, weakly reactive, (4A+), which are not affected in vitro by mAb 4A+C. In experiments where the proportion of Leu 2a-positive and Leu 3a-positive T cells were determined before and after treatment of peripheral T lymphocytes with mAb 4A+C, it was shown that the percentage of Leu 2a-positive and Leu 3a-positive cells were unchanged, but that the total T cell number was reduced by 55±4.6%. These data indicate that each of the two peripheral T lymphocyte cell lineages (i.e., the cytotoxic/suppressor lineage defined by leu 2a, and the inducer/helper cell lineage defined by Leu 3a) can be divided into a 4A+ population and a 4A++ population. This represents a new subset of T lymphocytes.

The 4A++ peripheral T cells contain the precursor T helper cells that are necessary for in vitro antibody production against SRBC and TNP. It is shown that the precursor T cell that proliferates in vitro in MLC is contained in the 4A+ T cell pool. The proliferative MLC response is unaffected by pretreatment of responder cells with mAb 4A+C, and the generation of the alloreactive cytotoxic T cell is also unaffected by this treatment. These results also indicate that the T cells that are necessary for in vitro generation of cytotoxic T cells are contained in 4A+ T cell pool. Furthermore, it is found that the alloreactive, cytotoxic T cells generated during in vitro MLC express 4A antigen, because they can be removed by mAb+C.

Studies using the FACS demonstrated that 4A+ T cells after in vitro activation with PHA and Con A express 4A antigen, and some of these will express 4A antigen in greater amounts than any of the 4A++ cells present in unactivated PBL. This increase of 4A antigen after mitogen stimulation, and the sensitivity of the alloactivated cytotoxic T cells to mAb+C, indicate that the 4A antigen may be a lymphocyte differentiation antigen that may be involved in cellular interactions.

Also, 4A may well be detecting a new cell line involved in hematopoietic interactions. Thus, 4A has use for diagnosis and/or immunotherapy against diseased hematopoietic cells as for instance, in Leukemia, or in disease where hematopoietic cells are involved or can be used for markers for the disease. Hematopoietic specimens can be diagnosed and treated. 4A has potential use in transplanation as for example use of 4A or a modified version of 4A (perhaps linked to toxin, Ricin etc.) to deplete T cells (e.g. helper and/or killer cells) and reduce graft versus host disease in bone marrow transplantation. 4A can be used in abnormal states as a diagnostic tool for ratios of helper to killer cells when such ratios are disturbed, as for example, in AIDS.

MAb 4A cuts across the three T cell antigen groupings as described above since it is found on killer T cells as well as helper T cells. Thus mAb 4A occupies a unique place in T cell systems.

Monoclonal antibody 4A is on deposit and available at Sloan-Kettering Institute, Human Immunogenetics Section, Department of Clinical Immunology, 1275 York Avenue, New York, N.Y. 10021.

4A has been deposited with the American Type Culture Collection (ATCC), 12301 Parklawn Drive, Rockville, Md. 20852 on Aug. 16, 1983 and has been given an ATCC accession number of HB8350.

What is claimed:

1. Monoclonal antibody 4A, characterized as an IgG2A, derived from immunization with normal, fresh, first stimulated, peripheral human T lymphocytes and capable of subsetting peripheral human T-cell populations comprising helper and killer T cells into a population having a strongly positive cytotoxic reaction with 4A+C which population comprises precursor helper T cells and a population having a more weakly reactive binding reaction with 4A+C which population shows increase of 4A antigen after a second mitogen stimulation.

2. Monoclonal antibody of claim 1 wherein the fresh, peripheral T-lymphocytes are stimulated with stimulants selected from the group consisting of PHA, conA and PWM.

3. Antibody producing hybridoma cell line derived from immunization with fresh peripheral, stimulated T-lymphocytes characterized by the production of monoclonal antibody 4A of claim 1.

4. Hybridoma cell line of claim 3 wherein the T-cells are stimulated with stimulants selected from the group consisting of pHA, Con A and PWM.

5. Method for subsetting human killer and human helper T-cells into weakly and strongly antigenic subsets which comprises
   (a) combining monoclonal antibody 4A with complement,
   (b) contacting cells selected from the group consisting of human killer and human helper T-cells populations and mixtures thereof with monoclonal antibody 4A and complement, and
   (c) counting percent affected cells.

* * * * *